United States Patent
Lee et al.

(10) Patent No.: US 9,669,103 B2
(45) Date of Patent: Jun. 6, 2017

(54) METAL-PARTICLE-BASED ORAL-ADMINISTRATING LIVER-SPECIFIC NUCLEIC ACID DELIVERY SYSTEM AND METHOD OF MANUFACTURING THE SAME

(71) Applicants: KOREA NATIONAL UNIVERSITY OF TRANSPORTATION Industry-Academic Cooperation Foundation, Chungcheongbuk-do (KR); THE CATHOLIC UNIVERSITY OF KOREA INDUSTRY-ACADEMIC COOPERATION FOUNDATION, Seoul (KR)

(72) Inventors: Yong Kyu Lee, Chungcheongbuk-do (KR); Sung Hoon Kang, Chungcheongbuk-do (KR); Sang Joon Lee, Gwangju (KR); In Kyu Park, Gwangju (KR); Kwang Jae Cho, Seoul (KR); Mohammed Nurunnabi, Chungcheongbuk-do (KR)

(73) Assignees: KOREA NATIONAL UNIVERSITY OF TRANSPORTATION INDUSTRY-ACADEMIC COOPERATION FOUNDATION, Chungcheongbuk-Do (KR); THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 15/074,443

(22) Filed: Mar. 18, 2016

(65) Prior Publication Data

US 2017/0065724 A1    Mar. 9, 2017

(30) Foreign Application Priority Data

Mar. 18, 2015   (KR) .................. 10-2015-0037342

(51) Int. Cl.
| | |
|---|---|
| C08B 37/08 | (2006.01) |
| C01G 7/00 | (2006.01) |
| C07H 21/02 | (2006.01) |
| C07H 21/04 | (2006.01) |
| A61K 31/7032 | (2006.01) |
| A61K 47/48 | (2006.01) |
| C12N 15/113 | (2010.01) |
| A61K 31/713 | (2006.01) |

(52) U.S. Cl.
CPC ........ *A61K 47/4823* (2013.01); *A61K 31/713* (2013.01); *A61K 47/48015* (2013.01); *C12N 15/113* (2013.01); *C12N 2310/14* (2013.01); *C12N 2310/351* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 6,509,154 B1 | 1/2003 | de Paillette | 435/6 |
| 9,133,454 B2 | 9/2015 | Kreutzer et al. | C12N 15/113 |

FOREIGN PATENT DOCUMENTS

| | | | | |
|---|---|---|---|---|
| WO | WO 99/07409 | 2/1999 | | A61K 38/21 |
| WO | WO 99/32619 | 7/1999 | | C12N 15/11 |
| WO | WO 00/44895 | 8/2000 | | C12N 15/11 |
| WO | WO 00/44914 | 8/2000 | | C12N 15/63 |
| WO | WO 01/29058 | 4/2001 | | C07H 21/04 |
| WO | WO 01/36646 | 5/2001 | | C12N 15/63 |

OTHER PUBLICATIONS

Bhattarai et al (J Nanopart Res (2008) 10:151-162, 2008).*
Lee et al (Journal of Controlled Release 51 (1998) 213-220).*
Sun et al (Angew. Chem. Int. Ed. 2011, 50, 9348 —9351).*
Kim et al (Biomacromolecules 2005, 6, 1154-1158).*
Huh et al (Journal of Controlled Release 144 (2010) 134-143).*
Sandstrom (Langmuir 2003, 19, 7537-7543).*
Bhumkar et al (Pharmaceutical Research, 24(8): 1415-1426, 2007).*

* cited by examiner

*Primary Examiner* — Richard Schnizer
(74) *Attorney, Agent, or Firm* — Harness, Dickey & Pierce, P.L.C.

(57) ABSTRACT

Disclosed are a metal-nanoparticle-based liver-specific nucleic acid delivery system, a method of manufacturing the same, and a liver disease treatment composition containing the same. The liver-specific nucleic acid delivery system is coated with a bile acid-glycol chitosan polymer, so that it provides excellent liver-tissue specificity and high absorbance through digestive canals. Since the nucleic acid of the nucleic acid delivery system is coated with the bile acid-glycol chitosan polymer, it can be protected from decomposition of enzymes and the like inside a living organism. The liver-specific nucleic acid delivery system can be developed as an oral-administrating liver-disease treatment.

14 Claims, 6 Drawing Sheets

SEQUENCE LISTING

```
<160> NUMBER OF SEQ ID NOS: 1

<210> SEQ ID NO 1
<211> LENGTH: 22
<212> TYPE: RNA
<213> ORGANISM: Artificial sequence
<220> FEATURE:
<223> OTHER INFORMATION: siRNA sequence which modified by SH-group in
      3' end

<400> SEQUENCE: 1
guccaguuuc ccaggaaucc cu                                              22
```

METAL-PARTICLE-BASED ORAL-ADMINISTRATING LIVER-SPECIFIC NUCLEIC ACID DELIVERY SYSTEM AND METHOD OF MANUFACTURING THE SAME

CROSS REFERENCES TO RELATED APPLICATIONS

This application claims the benefit and priority to Korean Patent Application No. 10-2015-0037342, filed in the Korean Patent Office on Mar. 18, 2015. The entire disclosure of the application identified in this paragraph is incorporated herein by reference.

FIELD

The present invention relates to a metal-nanoparticle-based liver-specific nucleic acid delivery system and a method of manufacturing the same.

BACKGROUND

There have been many studies in the art on therapeutic methods for cancer, such as a surgical operation, radiotherapy, chemotherapy, immunotherapy, and gene therapy. As one of them, small interfering ribonucleic acid (siRNA)-based therapy is a therapeutic method capable of silencing expression of a specific protein by bonding a siRNA to a messenger RNA (mRNA) of a RNA-induced silencing complex (RISC) and decomposing the bonding (see Non-patent Literatures 7 and 9). The siRNA-based therapy provides various solutions to genetic disorder diseases because of its repressor capability for effectively silencing expression of a target mRNA even with a small amount (see Non-patent Literatures 4 and 5). However, the siRNA is very unstable, so that it tends to decompose within a very short time inside a living organism. In addition, due to its anionic property, the siRNA does not easily penetrate through a negatively charged cell membrane and thus generates an endocytic problem (see Non-patent Literatures 7, 9, 10, and 16). In order to address the aforementioned problems, a viral delivery system has been proposed. However, this technique has some risks such as a nonspecific immune defense and some problems such as a complicated manufacturing process and is still not suitable for commercialization. Therefore, non-viral delivery systems using other types of delivery systems such as a cathionic lipid or a polymer material have been highlighted in the art. The nonviral delivery system is highly stable inside a living organism and inexpensive because of its easy manufacturing process. However, since the siRNA is small-sized and hard and has a weak anionic property, it is difficult to form a polymer complex disadvantageously (see Non-patent Literatures 10 and 13).

As means for addressing the aforementioned disadvantages of the siRNA, a nanostructure such as gold nanoparticles has been highlighted in the art. Gold nanoparticles have high biocompatibility and can be simply synthesized. In addition, it makes it possible to easily perform size control and surface modification (see Non-patent Literature 7).

If an end region of the siRNA is modified with a thiol group, the siRNA can be easily bonded to a gold nanoparticle. If the siRNA is modified and is then bonded to a gold nanoparticle, the siRNA is condensed on a surface of the gold nanoparticle, and shortcomings of the siRNA such as intrinsic hardness or a weak anionic property are eliminated, so that a polymer complex can be easily produced (see Non-patent Literatures 6 and 14).

If a cathionic polymer is used in an siRNA complex, it is possible to prevent decomposition of the siRNA inside a living organism and improve transmittance of an anionic cell membrane. A representative cathionic polymer used as an siRNA of the prior art is polyethylenimine (PH). However, it is known that cathionic polymers have cellular cytotoxicity for inducing apoptosis, and the cellular cytotoxicity increases as a molecular weight and a degree of branching of the polymer increases. Therefore, it is difficult to apply the cathionic polymer as an siRNA polymer complex for delivery to a living organism.

NON-PATENT LITERATURES

Non-patent Literature 1: R. N. Redinger, *Am. J. Surg.*, (2003), 185, 16872
Non-patent Literature 2: O. B. Ore, et al., *Magn. Reson. Med.*, (2005), 53, 14416
Non-patent Literature 3: R. M. Samstein, et al., *Biomaterials.*, (2008), 29,038
Non-patent Literature 4: A. Elbakry, et al., *Nano Lett.*, (2009), 9, 205964
Non-patent Literature 5: Y-K. Oh, et al., *Adv. Drug Deliv. Rev.*, (2009), 61, 85062
Non-patent Literature 6: A. Manuscript, *NIH Public Access.*, (2010), 131,) 20723
Non-patent Literature 7: M. Lee, et al., *Nanocomplex*, (2011) 61386147
Non-patent Literature 8: F Li, et al., *Mater. Sci. Eng. C.*, (2012), 32, 201725
Non-patent Literature 9: L. C. Gomes-da-silva, et al., *Acc. Chem. Res.*, (2012), 45, 116371
Non-patent Literature 10: S. J. Lee, et al., *Angew. Chem. Int. Ed. Engl*, (2012), 51, 72037
Non-patent Literature 11: H. Sung, et al., *Acc. Chem. Res.*, (2012), 45, 61929
Non-patent Literature 12: Z. Khatun, et al., *J. Control. Release.*, (2013), 170, 7482
Non-patent Literature 13: K. Park, et al., *Bioconjugate Chem.*, (2013), 24(7), pp 12019
Non-patent Literature 14: S. Son, et al., *ACS Nano*, (2014), 8 (6), 557484
Non-patent Literature 15: Z. Khatun, et al., *J. Control. Release.* (2014), 177, 6473
Non-patent Literature 16: H. J. Kim, et al., *G. Nanoparticles* (2014) 897991

SUMMARY

The inventors made diligent efforts to develop a nucleic acid molecule delivery system capable of providing organo-specificity, stability of nucleic acid molecules, excellent organism absorption. As a result, the inventors successfully developed a nucleic acid delivery system having liver-specificity and improved stability of nucleic acid molecules inside a living organism by using gold nanoparticles, glycol chitosan, and taurocholic acid, and experimentally demonstrated liver-specificity to embody the present invention.

In view of the aforementioned problem, it is an object of the present invention to provide a metal-nanoparticle-based liver-specific nucleic acid delivery system.

It is another object of the present invention to provide a pharmaceutical composition for treating liver diseases including a pharmaceutically effective dose of the metal-nanoparticle-based liver-specific nucleic acid delivery system.

It is still another object of the present invention to provide a method of manufacturing a metal-nanoparticle-based liver-specific nucleic acid delivery system.

According to an aspect of the present invention, there is provided a metal-nanoparticle-based liver-specific nucleic acid delivery system including: (a) a metal nanoparticle; (b) a nucleic acid molecule bonded to a surface of the metal nanoparticle; and (c) a bile acid-glycol chitosan polymer attached to the nucleic acid molecule.

According to another aspect of the present invention, there is provided a liver disease treatment pharmaceutical composition containing a pharmaceutically effective amount of the nucleic acid delivery system.

According to still another aspect of the present invention, there is provided a method of manufacturing a metal-nanoparticle-based liver-specific nucleic acid delivery system, the method including: (a) bonding a nucleic acid molecule to a surface of a metal nanoparticle; (b) reacting bile acid and glycol chitosan to produce a bile acid-glycol chitosan polymer; and (c) attaching the produced bile acid-glycol chitosan polymer to the metal nanoparticle having the surface where the nucleic acid molecule is bonded.

Preferably, the nucleic acid molecule may be bonded to the surface of the metal nanoparticle by using a thiol group (—SH).

Preferably, the metal nanoparticle may include a gold nanoparticle, a silver nanoparticle, or a magnetic nanoparticle.

Preferably, the nucleic acid molecule may be at least one molecule selected from a group consisting of deoxyribonucleic acid (DNA), ribonucleic acid (RNA), small interfering RNA (siRNA), antisense nucleic acid, nucleic acid aptamer, ribosome, polynucleotide, and oligonucleotide.

Preferably, the bile acid may be at least one acid selected from a group consisting of deoxycholic acid, taurodeoxycholic acid, taurocholic acid, and glycochenodeoxyhoclic acid.

Preferably, the bile acid-glycol chitosan polymer may be formed by covalent bonding between bile acid and glycol chitosan.

Preferably, the bile acid-glycol chitosan polymer may be positively charged.

Preferably, a conjugation ratio between glycol chitosan and bile acid of the bile acid-glycol chitosan polymer may be set to 1:1 to 1:100 as a molar ratio.

Other objects and technical characteristics of the present invention will become apparent by reading the following description, claims, and drawings.

BRIEF DESCRIPTION OF THE DRAWINGS

The foregoing and additional features and characteristics of this disclosure will become more apparent from the following detailed description considered with reference to the accompanying drawings, wherein.

DETAILED DESCRIPTION

Figure 1:
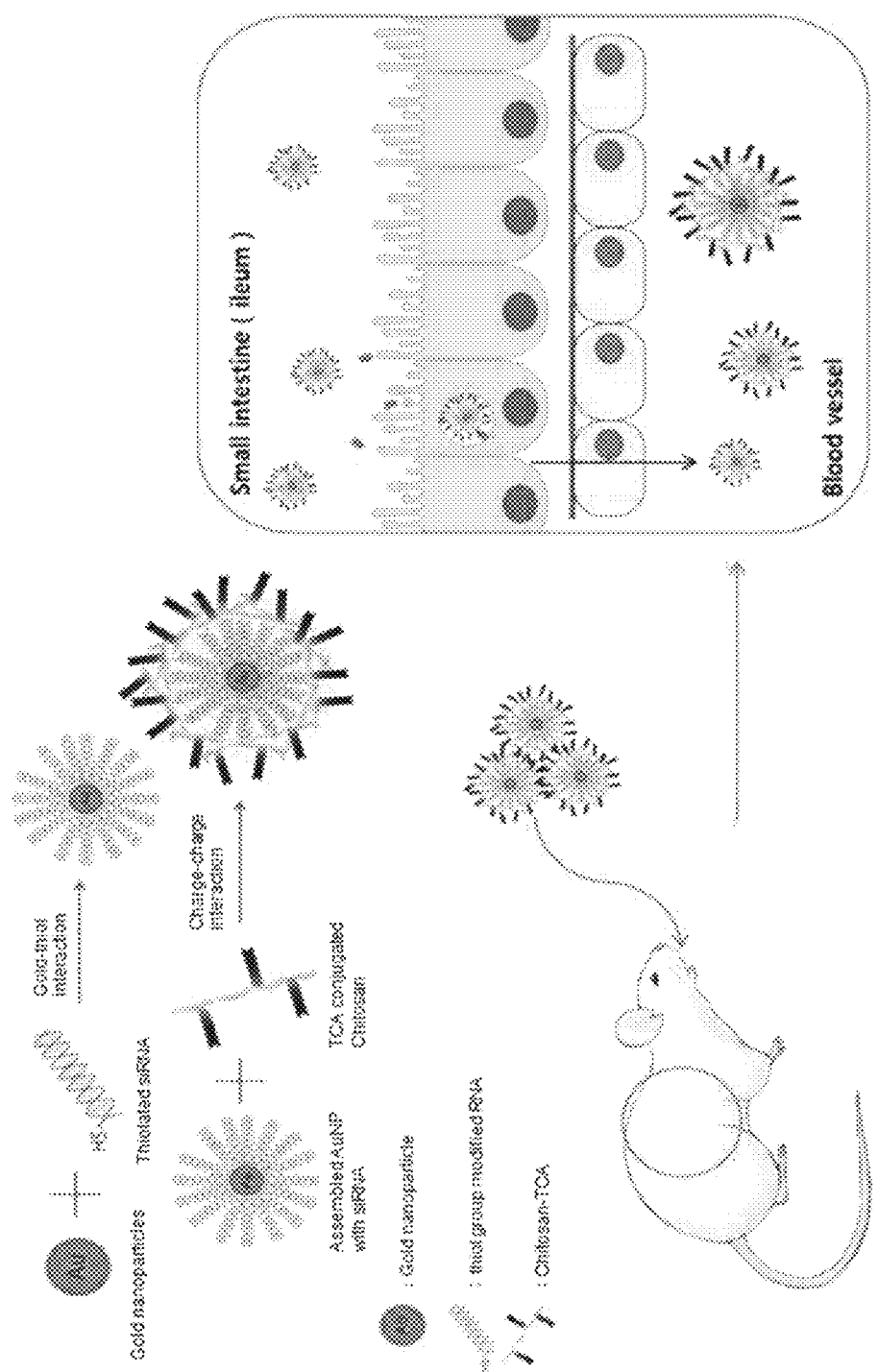
FIG. 1 is a schematic diagram illustrating a concept of the present invention.

A description will now be made for a metal-nanoparticle-based liver-specific nucleic acid delivery system according to the present invention with reference to the accompanying drawings in more detail.

A metal-nanoparticle-based liver-specific nucleic acid delivery system according to the present invention includes: (a) a metal nanoparticle; (b) a nucleic acid molecule bonded to a surface of the metal nanoparticle; and (c) a bile acid-glycol chitosan polymer attached to the nucleic acid molecule.

The metal nanoparticle according to the present invention may include any type of metal particles having a metal property and a nanometer scale diameter, such as gold, silver, platinum, palladium, and iron, without limiting thereto. The metal nanoparticle has a nanometer scale diameter, preferably 8 to 100 nm, more preferably 10 to 50 nm, and most preferably 12 to 14 nm. However, any metal particle may also be employed as long as it has a nanometer scale particle size.

According to an embodiment of the present invention, the metal nanoparticle includes a gold nanoparticle, a silver nanoparticle, or a magnetic nanoparticle.

Specifically, the metal nanoparticle may be a gold nanoparticle.

The gold nanoparticle has a stable particle shape and can be easily manufactured. In addition, its size can be easily controlled, and it has biocompatibility and human harmlessness.

The gold nanoparticle according to the present invention may be produced by reducing $HAuCl_4$ by using $HAuCl_4$ as a gold source and using sodium citrate as a reductant. The size of the produced gold particle can be controlled depending on the amount of citrate as a reductant. As the amount of the added citrate as a reductant increases, nucleation for producing gold nanoparticles is more promoted. Consequently, the size of the gold nanoparticle is reduced.

If the gold nanoparticle has a diameter equal to or larger than 100 nm, it is difficult to bond the gold nanoparticle to a functional group such as a thiol group or an amine group, and a nanoparticle property such as endocytosis is easily removed. Therefore, the gold nanoparticle according to the present invention preferably has a diameter smaller than 100 nm.

The nucleic acid molecule is bonded to the surface of the metal nanoparticle.

The nucleic acid molecule has an additional functionality for bonding to the surface of the metal nanoparticle.

The functional group may include a thiol group or an amine group and may be positioned in a 3' end region of the nucleic acid.

According to an embodiment of the present invention, the nucleic acid molecule has a thiol group as a functional group and is bonded to a surface of the metal nanoparticle by using a thiol group.

If the nucleic acid molecule is bonded to the surface of the metal nanoparticle, an anionic property increases due to the nucleic acid molecule, so that bonding to a cathionic polymer is facilitated.

According to an embodiment of the present invention, the nucleic acid molecule is at least one molecule selected from a group consisting of deoxyribonucleic acid (DNA), ribonucleic acid (RNA), small interfering RNA (siRNA), anti-sense nucleic acid, nucleic acid aptamer, ribosome, polynucleotide, and oligonucleotide.

Specifically, the nucleic acid according to the present invention is siRNA.

The siRNA is a nucleic acid molecule capable of mediating RNA interference or gene silencing (see WO00/44895, WO01/36646, WO99/32619, WO01/29058, WO99/07409, and WO00/44914). Since the siRNA can suppress expression of a target gene, it is employed in an effective gene knock-down method or a gene therapeutic method.

The siRNA molecule according to the present invention may have a short nucleotide sequence (for example, approximately 5 to 15 nt) inserted between self-complementary sense and anti-sense strands. In this case, the siRNA molecule generated by expression of the nucleotide sequence forms a hairpin structure due to hybridization and thus generally forms a stem-and-loop structure. This stem-and-loop structure is processed in vitro or in vivo to generate active siRNA molecules capable of mediating RNA interference (RNAi).

The metal nanoparticle having a surface where the nucleic acid molecule is bonded according to the present invention is coated with the bile acid-glycol chitosan polymer. This coat is formed by attaching the bile acid-glycol chitosan polymer to the nucleic acid molecule bonded to a surface of the metal nanoparticle. The attachment between the bile acid-glycol chitosan polymer and the nucleic acid molecule is preferably formed by an electrostatic attractive force generated between positively and negatively charged substances.

Herein, the terminology "bile acid-glycol chitosan polymer" refers to a polymer compound obtained by linking bile acid and glycol chitosan.

According to an embodiment of the present invention, the "bile acid-glycol chitosan polymer" has a covalent bond between bile acid and glycol chitosan.

Herein, the terminology "bile acid" refers to "steroid acid" contained predominantly in the bile of mammals.

The bile acid may use enterohepatic circulation. As a result, it is possible to improve delivery performance of the nucleic acid delivery system according to the present invention to liver organs.

According to an embodiment of the present invention, the bile acid is at least an acid selected from a group consisting of deoxycholic acid, taurodeoxycholic acid, taurocholic acid, and glycochenodeoxyhoclic acid.

Herein, the glycol chitosan as a positive charge substance makes it possible to attach the "bile acid-glycol chitosan polymer" to the metal nanoparticle, where the nucleic acid molecule is bonded, by virtue of an electrostatic attractive force.

According to the present invention, the glycol chitosan improves absorption of the nucleic acid delivery system of the present invention through digestive canals in the case of oral administration and prevents decomposition of nucleic acid molecules from enzymes existing in the digestive canal.

According to an embodiment of the present invention, the bile acid-glycol chitosan polymer is positively charged.

The entire charge amount of the bile acid-glycol chitosan polymer can be adjusted by controlling a composition between the bile acid and the glycol chitosan.

According to an embodiment of the present invention, a conjugation ratio between glycol chitosan and bile acid of the bile acid-glycol chitosan polymer is set to 1:1 to 1:100 (molar ratio), and more preferably, 1:50 to 1:100.

A description will now be made for a pharmaceutical composition for treating a liver disease including a pharmaceutically effective dose of the nucleic acid delivery system according to another aspect of the present invention.

Herein, the terminology "pharmaceutically effective dose" refers to the amount of the nucleic acid delivery system by which a liver disease can be treated effectively and sufficiently.

Herein, the liver disease includes acute a hepatitis, a chronic hepatitis, a hepatocirrhosis, a liver cirrhosis, a fatty liver, or a liver cancer, but not limited thereto.

Pharmaceutically allowable carriers contained in the pharmaceutical composition according to the present invention and used commonly during preparation include lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, propyl hydroxybenzoate, talc, magnesium stearate, mineral oil, or the like, but not limited thereto. The pharmaceutical composition according to the present invention may further contain, in addition to the elements described above, a lubricating agent, a wetting agent, a sweetening agent, a flavor agent, an emulsion, a suspension, a preservative agent, or the like. Suitable carriers and agents pharmaceutically allowable are described in *Remington's Pharmaceutical Sciences* (19th ed., 1995) in detail.

A proper administration dose of the pharmaceutical composition according to the present invention may be prescribed in various manners depending on some factors such as a formulation method, an administration method, a patient's age, weight, and sexuality, or a disease condition, foods, an administration time, an administration path, an excretion time, and response sensitivity. Meanwhile, an administration dose of the pharmaceutical composition according to the present invention is preferably set to 0.001 to 1000 mg/kg (patient's weight) per day.

The pharmaceutical composition according to the present invention may be administered either orally or non-orally. In the case of the non-oral administration, it may be administered through intravenous injection, hypodermic injection, intramuscular injection, abdominal cavity injection, transdermal delivery, and the like. Preferably, the nucleic acid delivery system according to the present invention is administered orally.

A concentration of activated components contained in the composition according to the present invention is determined considering a treatment purpose, a patient's condition, a necessary time period, a disease severity level, and the like, and is not limited to a certain range of the concentration.

The pharmaceutical composition according to the present invention is formulated by using carriers and/or excipients pharmaceutically allowed by a person skilled in the art, so that it can be manufactured in a unit capacity type or in a large-capacity integration type. In this case, the formulation type may include a solution type in oil or an aqueous medium, a suspension type, an emulsion type, an extract type, a powder type, a granule type, a tablet type, or a capsule type. In addition, the composition may further include a dispersant or a stabilizer.

A description will now be made for a method of manufacturing a metal-nanoparticle-based liver-specific nucleic acid delivery system. The method has the following processes.
  (a) process of bonding a nucleic acid molecule to a surface of a metal nanoparticle;
  (b) process of reacting bile acid and glycol chitosan to produce a bile acid-glycol chitosan polymer; and
  (c) process of attaching the produced bile acid-glycol chitosan polymer to the metal nanoparticle having the surface where the nucleic acid molecule is bonded.

A description will now be made for the (a) process of bonding a nucleic acid molecule to a surface of a metal nanoparticle.

First, a reactive solution containing metal nanoparticles is prepared, and nucleic acid molecules are added to the prepared reactive solution to generate bonding.

According to an embodiment of the present invention, the metal nanoparticle may include a gold nanoparticle, a silver nanoparticle, or a magnetic nanoparticle. Preferably, the metal nanoparticle is a gold nanoparticle.

According to another embodiment of the present invention, the nucleic acid molecule is bonded to the surface of metal nanoparticle by using a thiol group (—SH).

The nucleic acid molecule may be bonded to the surface of the metal nanoparticle by reacting a sufficient amount with the metal nanoparticles.

A molar ratio between the metal nanoparticles and the nucleic acid molecules during bonding therebetween is not particularly limited and may be suitably selected by a person skilled in the art. Preferably, the molar ratio between the metal nanoparticles and the nucleic acid molecules in the bonding reaction is set to "1:1 to 1:300", and more preferably, "1:1 to 1:200."

According to another embodiment of the present invention, the nucleic acid molecule may include deoxyribonucleic acid (DNA), ribonucleic acid (RNA), small interfering RNA (siRNA), anti-sense nucleic acid, nucleic acid aptamer, ribosome, polynucleotide, or oligonucleotide. Preferably, the nucleic acid molecule is siRNA.

A description will now be made for the (b) process of reacting bile acid and glycol chitosan to produce a bile acid-glycol chitosan polymer.

Each of bile acid and glycol chitosan is dissolved to distilled water to make respective solutions. Then, both solutions are mixed and reacted to produce a bile acid-glycol chitosan polymer by conjugating the bile acid and the glycol chitosan.

According to an embodiment of the present invention, the bile acid may be selected from a group consisting of deoxycholic acid, taurodeoxycholic acid, taurocholic acid, and glycochenodeoxyhoclic acid. Preferably, the bile acid is taurocholic acid.

According to an embodiment of the present invention, the bile acid-glycol chitosan polymer is generally positively charged.

According to another embodiment of the present invention, a feed ratio between glycol chitosan and bile acid in production of the bile acid-glycol chitosan polymer is set to 1:1 to 1:100, and preferably, 1:50 to 1:100 as a molar ratio.

A description will now be made for the (c) process of attaching the produced bile acid-glycol chitosan polymer to the metal nanoparticle having a surface where the nucleic acid molecule is bonded.

The produced metal nanoparticle having a surface where the nucleic acid molecule is bonded and the produced bile acid-glycol chitosan polymer are mixed in a suitable solvent, and the polymer is attached to the metal nanoparticle. The bile acid-glycol chitosan polymer is generally positively charged, and the metal nanoparticle having a surface where the nucleic acid molecule is bonded is negatively charged. Therefore, the polymer is attached to the metal nanoparticle by virtue of an electrostatic attractive force.

A description will now be made for advantageous effects of the present invention.
  (i) The present invention relates to a metal-nanoparticle-based liver-specific nucleic acid delivery system, a method of manufacturing the same, and a liver disease treatment composition containing the same.
  (ii) The liver-specific nucleic acid delivery system according to the present invention is coated with the bile acid-glycol chitosan polymer, so that it can provide excellent liver specificity and high absorption through digestive canals.
  (iii) The nucleic acid as an effective component of the liver-specific nucleic acid delivery system according to the present invention is coated with the bile acid-glycol chitosan polymer, so that it can be protected from decomposition caused by enzyme and the like inside a living organism.
  (iv) The liver-specific nucleic acid delivery system according to the present invention can be developed as an oral-administrating liver disease treatment.

EXAMPLES

Experiment Materials and Method

1. Experiment Materials

As experiment materials, glycol chitosan (GC), taurocholic acid (TCA), 4-niitrophenyl chloroformate (4-NPC), triethylamine (TEA), gold(III) chloride hydrate (HAuCl$_4$), trisodium citratedehydrate, diethylpyrocarbonate (DEPC), a HEPES buffer, and NaCl were purchased from Sigma-Aldrich Co. LLC. An siRNA modified with a thiol group (siRNA-SH, Sequence: 5'-GUCCAGUUUCCCAG-GAAUCCCU None-3': Sequence No. 1) was purchased from ST Pharm Oligo Center. BALB/c nude mice 6 to 7 weeks old were purchased from Orient Bio Inc.

2. Production of GC-TCA Polymer

First, a glycol chitosan (GC) solution was prepared by perfectly dissolving glycol chitosan in distilled water. A taurocholic acid (TCA) solution was prepared by perfectly dissolving taurocholic acid in distilled water, and a temperature was controlled to 0 to 4° C. A 4-NPC solution was prepared by dissolving 4-niitrophenyl chloroformate in dimethyl sulfoxide (DMSO). The 4-NPC solution was added to the TCA solution, and triethylamine (TEA) was then added in drops. In this case, the solution has a perfectly transparent yellow color. In this state, the solution was stirred for 30 minutes, and was additionally stirred for 1 hour. The GC solution was added to the prepared TCA solution, and the mixed solution was stirred for 24 hours to generate reaction. The solution subjected to the reaction was dialyzed by using a membrane filter having a molecular weight cut off (MWCO) of 1 kDa for 24 hours while exchanging distilled water every 3 hour. As the color of the solution changes from yellow to transparent, lyophilization was performed to obtain a GT polymer powder by conjugating GC and TCA. The obtained GT polymer was retained in a refrigerator at a temperature of 4° C. before use.

3. Synthesis of Gold Nanoparticles (AuNP)

Every glass device used in the synthesis of AuNP was cleaned before use by using aqua regia obtained by mixing nitric acid and hydrochloric acid by a weight percentage of 1:3. A $HAuCl_4$ solution (10 mg/ml) of 2 ml was added to distilled water of 100 ml heated to a temperature of 97.5° C., and was stirred for 30 minutes. After 30 minutes, trisodium citrate of 73.524 mg was dissolved to distilled water at minimum, and a $AuCl_4$ solution was added. Then, stirring was performed strongly for 30 minutes. When the color of this solution changed from transparent to red, heating stopped, and stirring was performed further for 30 minutes. The produced solution was cooled and retained in a room where all light is blocked out at a temperature of 4° C.

4. DEPC Treatment of AuNP, siRNA Bonding, and Coating with Glycol Chitosan or Glycol Chitosan-Taurocholic Acid Polymer Diethylpyrocarbonate (DEPC) having a total volume fraction of 0.1% was added to the AuNP solution stabilized by citrate, and the resulting solution was sufficiently stirred for 12 hours. Then, pressurized sterilization was performed at a temperature of 121° C. for 60 minutes to prepare AuNP processed with the DEPC. The siRNA modified with a thiol group and the AuNP treated with DEPC were mixed by suitably controlling the molar ratio, and the resulting mixture was reacted at a temperature of 4° C. for 12 hours. After the reaction, a NaCl solution (1 M) was added to form a salt solution condition of 0.1 to 0.3 M. The siRNA-bonded AuNP solution was centrifuged at a centrifugal force of 15,000×g for 15 minutes to remove non-bonded siRNAs, and the resulting solution was re-suspended with a HEPES buffer (see Non-patent Literatures 6, 14, and 16). The aforementioned process was repeated three times to remove non-bonded siRNAs as many as possible. Then, re-suspension was performed by using a GC solution or a GT polymer solution, and the re-suspended solution was reacted at a temperature of 4° C. for 1 hour. After this reaction, centrifugation was performed at a centrifugal force of 15,000×g for 15 minutes to remove non-bonded polymers, and the resulting solution was re-suspended by using a HEPES buffer. The aforementioned process was repeated three times, and lyophilization was performed to obtain a dried sample (see Non-parent Literatures 7 and 10).

5. Visualization of Oral Administration Absorption Path of Nucleic Acid Delivery System in vivo BALB/c nude mice 6 to 7 weeks old were starved for one day before administration of experiment drugs to prevent noise that may be generated by any food inside stomachs. In addition, glycol chitosan (GC) colored with rhodamine B and AuNP coated with a GT polymer having a different conjugation ratio (molar ratio) between GC and TCA were orally administered to the nude mice. Then, fluorescent images of the mice were captured by using Kodak™ Image Station every 3 hour. After 12 hours of the oral administration, the mice were anatomized, and fluorescent images were captured for internal organs such as stomachs, small intestines, livers, hearts, lungs, kidneys to check absorbance of each organ. Then, the weights of each organ were measured, and the organs were homogenized by adding phosphate-buffered saline (PBS) having a concentration of 100 g/L. A suspension obtained after the homogenizing was centrifuged, and an upper layer liquid was collected. Then, a fluorescence degree was measured by using Varioskan™ Flash Multimode Reader.

Results of Experiment

1. Characteristics of Produced AuNP

In order to check formation of anionic AuNP stabilized by trisodium citrate, a ultraviolet-visible (UV-VIS) spectroscopic analysis, a zeta-potential analysis, a dynamic light scattering (DLS) analysis, a scanning electron microscope (SEM) analysis, and a transmission electron microscope (TEM) analysis were performed.

Figure 2:
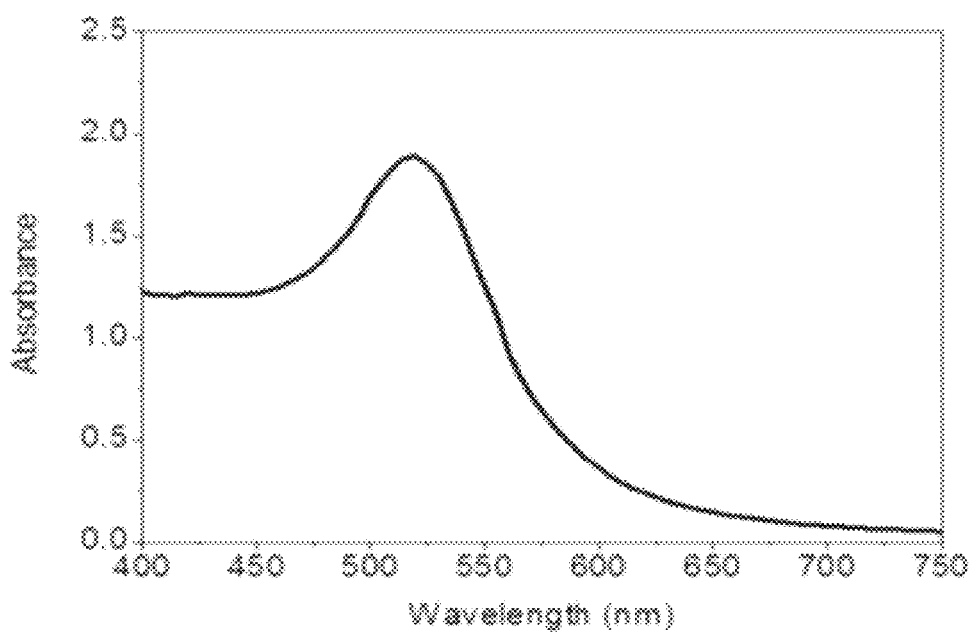
FIG. 2 is a graph illustrating a result of UV-VIS spectroscopy for produced gold nanoparticles (AuNP), which shows maximum absorbance at a wavelength of 520 nm.
Figure 3:
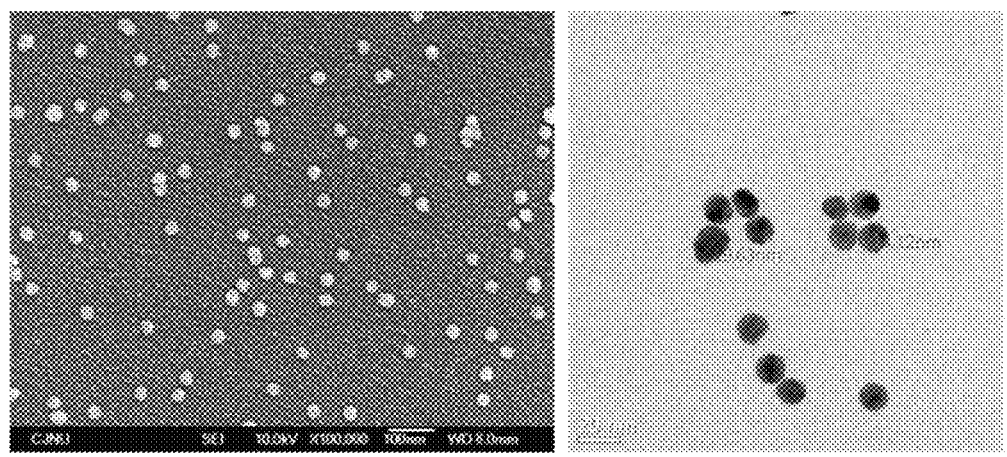
FIG. 3 is microscopic images illustrating experiment results for the produced AuNP, in which the left image is captured by using an scanning electron microscope image, and the right image is captured by using a transmission electron microscope.

As a result of the UV-VIS spectroscopic analysis for most basically checking formation of gold nanoparticles, it was observed that AuNP absorbs light at a wavelength of 520 nm (refer to FIG. 2). In addition, DLS, SEM, and TEM analyses were performed to check sizes and shapes of nanoparticles and whether or not agglutination occurs. The results thereof are shown in FIG. 2. First, the DLS value of AuNP was 18.25±1.51 nm, and the same result was obtained in the SEM and TEM analyses (refer to FIG. 3). As a result, it was recognized that the produced AuNP molecules are distributed in a single molecule state without being agglutinated. The AuNP stabilized by trisodium citrate is negatively charged due to the trisodium citrate. In order to confirm this fact, the zeta potential was measured. As a result, it was found out that the produced AuNP has a zeta potential of −13±1.38 mV, which is anionic.

2. Production Result and Characteristics of GC-TCA Polymer

Figure 4:
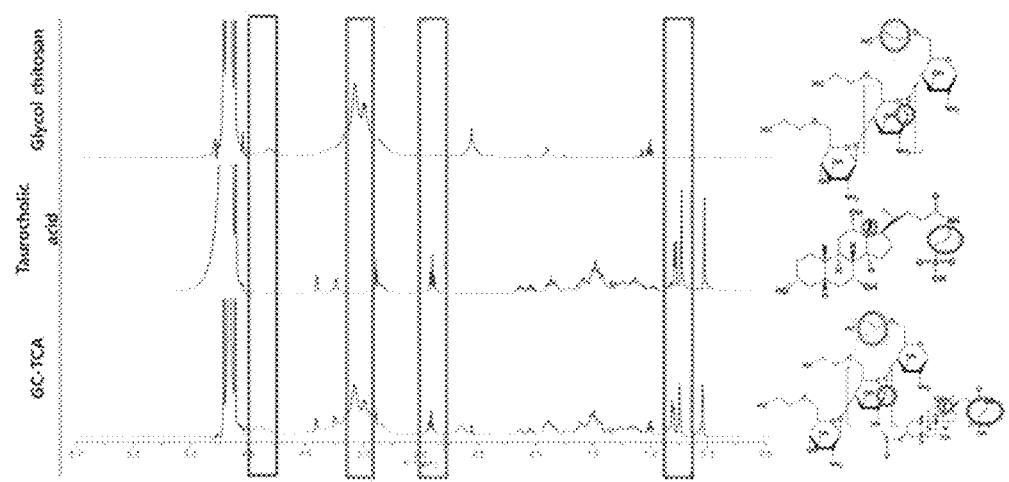
FIG. 4 illustrates hydrogen nuclear magnetic resonance spectroscopy (H-NMR) spectrum images of glycol chitosan (GC), taurocholic acid (TCA), and a glycol chitosan-taurocholic acid polymer (GC-TCA polymer)

In order to produce the GC-TCA polymer, an amine group of glycol chitosan and a hydroxyl group of taurocholic acid were conjugated by using 4-NPC and TEA, and the GC-TCA conjugation was analyzed through H-NMR spectroscopy (refer to FIG. 4). The peaks corresponding to GC in the H-NMR graph were observed at 4.4 and 3.5 ppm, and the peaks corresponding to TCA in the H-NMR graph were observed at 2.8 and 0.75 ppm. In the case of the GT polymer graph of FIG. 4, the peaks were observed in the same positions (see Non-patent Literature 2).

Table 1 shows GC-TCA conjugation ratios and zeta potentials of the synthesized GT polymer. The GC-TCA conjugation ratio was obtained by measuring the number of primary amine groups of glycol chitosan reduced by conjugation between the primary amine group of GC and TCA through a 2,4,6-trinitrobenzene sulfonic acid (TNBSA) assay. As a result, it was found out that, when a feed ratio (molar ratio) between GC and TCA increases to "1:50," "1:100," "1:200," and "1:300," the conjugation ratio (molar ratio) between GC and TCA also increases to "42.80±0.35," "94.77±0.22," "152.05±0.21," and "162.60±0.13," respectively.

The GC not conjugated with TCA has a zeta potential of 45.90±0.1 mV, which is a considerably positive charge state. However, if GC and TCA are conjugated, and the number of the conjugated TCAs increases, the zeta potential changes to "29.51±1.70 mV," "0.44±0.37 mV," "−8.31±0.13 mV," and "−27.11±0.21 mV," which gradually comes close to a neutral charge state. It was found out that, if the conjugation ratio becomes equal to or higher than "1:150," it is strongly negatively charged. Based on the experiment described above, the inventors selected a positively charged GT polymer that can be bonded to AuNP where strongly negatively charged siRNAs are bonded. The selected GT polymers are described in Sample Nos. 1, 2, and 3 in the following Table 1.

TABLE 1 sample No.
feed ratio
conjugation ratio
zeta potential

3. Production of siRNA-bonded AuNP and Analysis of Characteristics Thereof

RNase-free AuNP was produced by processing DEPC. Then, the siRNA modified with a thiol group (siRNA-SH) was bonded to the produced AuNP. Differences were analyzed by using DLS values and the zeta potentials. A DLS experiment was performed for siRNA-bonded AuNP and non-siRNA-bonded AuNP. As a result, it was found out that the size of AuNP slightly increases from "18.25±1.51 nm" to "21.85±1.08 nm" through the siRNA bonding. Since the siRNA has a very small size, the result does not exhibit a significant difference. However, it was recognized that the size increases due to the siRNA bonding. In order to analyze electrical characteristics of the siRNA-bonded or non-siRNA-bonded AuNP, the zeta potentials were analyzed. The siRNA and the AuNP have zeta potentials "−7.29±4.86 mV" and "−13±1.38 mV," respectively, both of which are insignificantly negative charge states. However, it was recognized that, as a result of the bonding between AuNP and siRNA, if the bonding ratio (AuNP:siRNA) increases to "1:10," "1:50," and "1:100," the zeta potential changes to "−23.23±1.16 mV," "−26.35±1.80 mV," and "−28.60±0.90 mV," respectively (refer to Table 2).

TABLE 2 sample
feed ratio
zeta potential

4. Production of AuNP-siRNA-GC or AuNP-siRNA-GT Delivery System and Characteristics Thereof The following Table 3 shows DLS values and zeta potentials measured after coating the GC or the GT polymer to AuNP bonded with siRNA at a bonding ratio (molar ratio) of 1:100.

TABLE 3

AuNP-based siRNA polymer
coat material
zeta potential
glycol chitosan
glycol chitosan-taurocholic acid
glycol chitosan-taurocholic acid As a result of the measurement, the DLS values of the AuNP-siRNA polymer coated with GC, GT50, or GT100 was "58.52±9.69 nm," "99.26±3.21 nm" or "114.83±1.66 nm," respectively. This shows that, as the TCA conjugation ratio of the GT polymer increases, the diameter of the nanoparticle increases. As the conjugation of TCA increases, the positive charge of the GC is weakened, so that charge-interaction with the negatively charged AuNP-siRNA polymer is weakened. As a result, particles are strongly agglutinated, and a force of forming small particles becomes short. Referring to the zeta potentials of Table 1, as the amount of TCA conjugated with GC increases, the zeta potential is definitely reduced.

Figure 5:
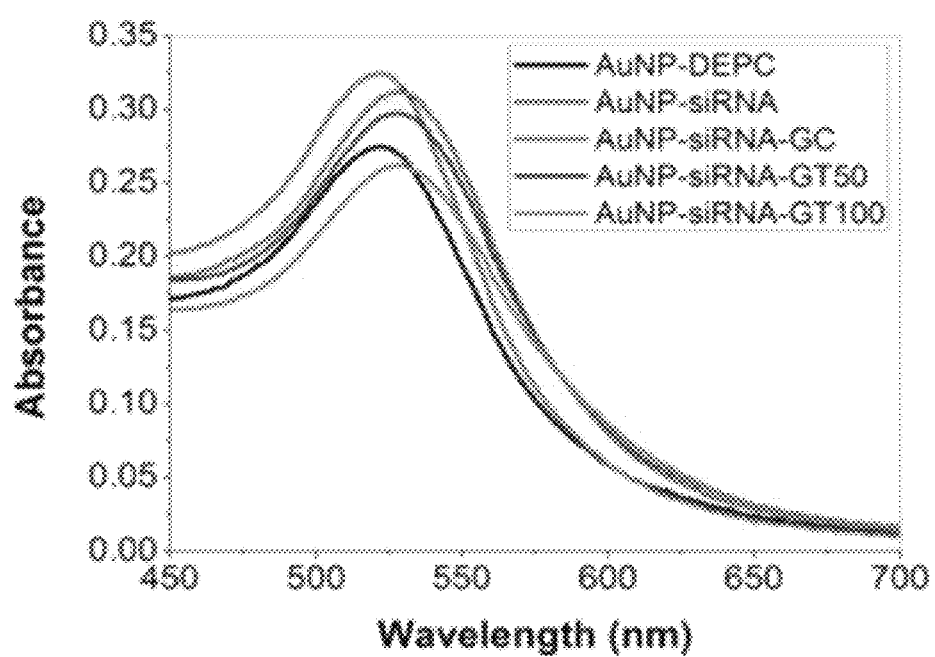
FIG. 5 illustrates results of UV-VIS spectroscopy for AuNP-DEPC, AuNP-siRNA, AuNP-siRNA-GC, AuNP-siRNA-GT50, and AuNP-siRNA-GT100.

FIG. 5 is a graph illustrating results of the UV-VIS spectroscopic analysis for AuNP-DEPC, AuNP-siRNA, AuNP-siRNA-GC, AuNP-siRNA-GT50, and AuNP-siRNA-GT100. Through the experiment described above, it is possible to recognize how much agglutination of AuNP can be controlled when siRNA, siRNA, GC, or GT polymer is bonded to AuNP to produce a resulting delivery substance. As a result, in the case of AuNP-siRNA obtained by bonding AuNP and siRNA, it was observed that a peak absorbance was exhibited at a wavelength of 522 nm, where no agglutination occurs, and siRNA is bonded to AuNP. In the case of AuNP-siRNA-GC, AuNP-siRNA-GT50, and AuNP-siRNA-GT100, it was recognized that a peak absorbance is exhibited at a wavelength of 528 nm, which is shifted to the right by approximately 6 nm from the wavelength of the existing gold nanoparticles (522 nm). This value is very small value. As a result, it was recognized that the final product was synthesized stably without agglutination of AuNP.

Figure 6:
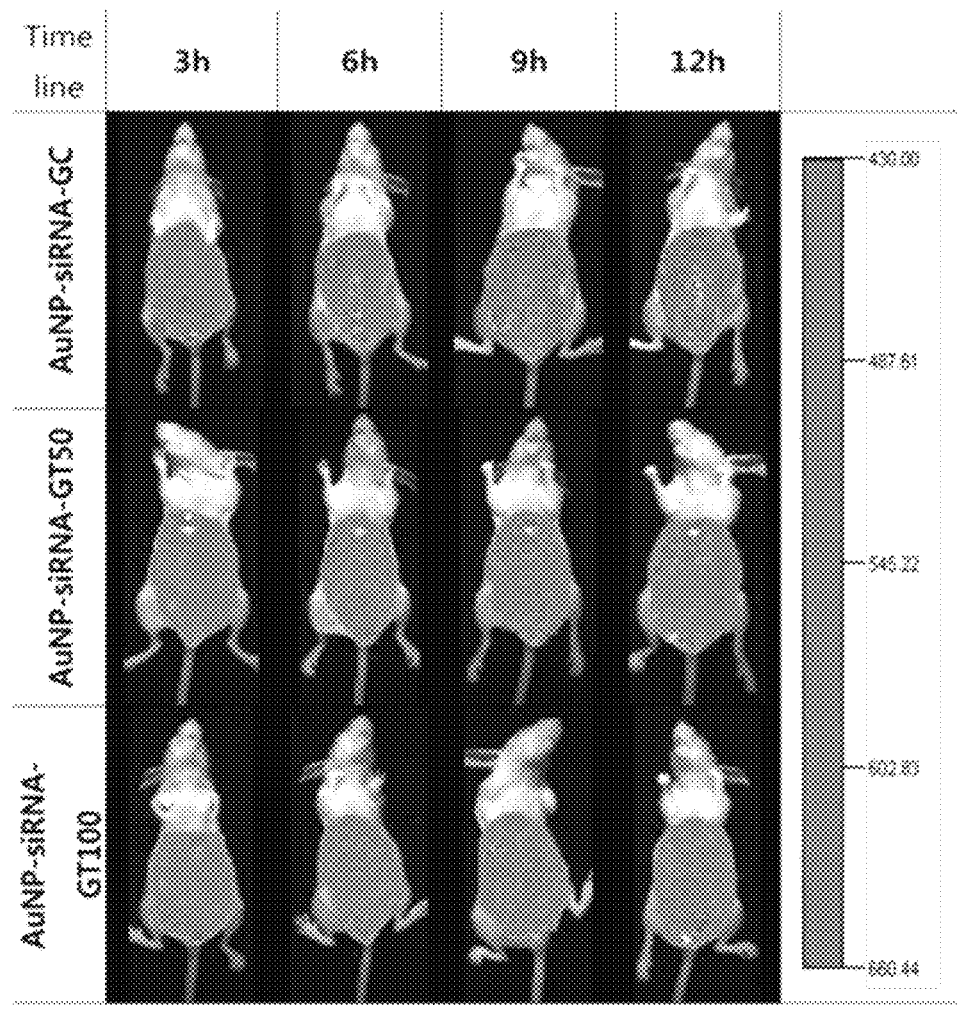
FIG. 6 illustrates fluorescent images of nude mice captured after 12 hours by orally administrating AuNP-siRNA-GC, AuNP-siRNA-GT50, and AuNP-siRNA-GT100 mixed with fluorescent materials.
Figure 7:
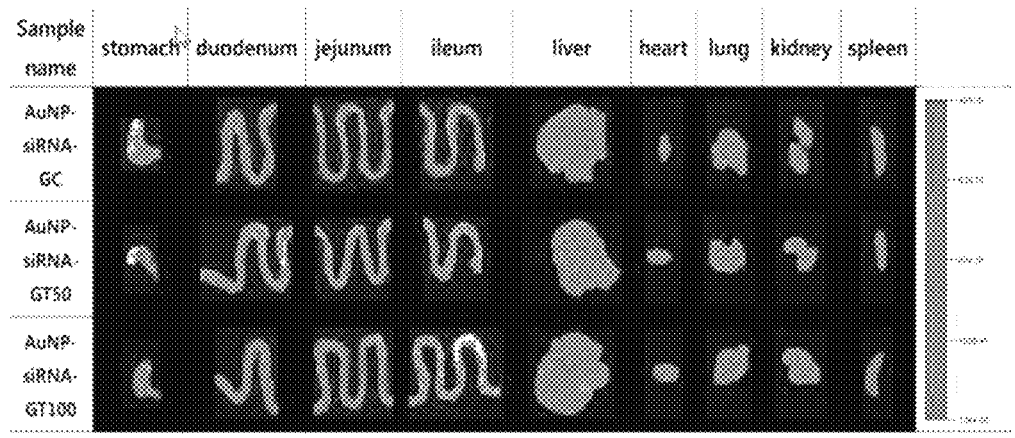
FIG. 7 illustrates ex-vivo fluorescent images of nude mice captured after 12 hours by orally administrating AuNP-siRNA-GC, AuNP-siRNA-GT50, and AuNP-siRNA-GT100 mixed with fluorescent materials.
Figure 8:
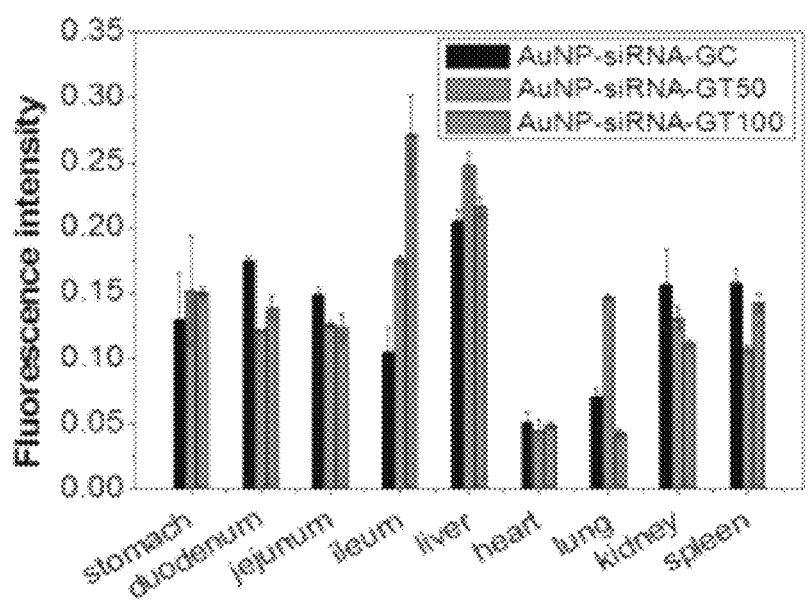
FIG. 8 illustrates fluorescence intensities of each organ of nude mice analyzed after 12 hours by orally administering AuNP-siRNA-GC, AuNP-siRNA-GT50, and AuNP-siRNA-GT100 mixed with fluorescent materials.

5. Analysis of Oral Administration and Absorption Path of AuNP-siRNA-GC or AuNP-siRNA-GT Delivery System How much the AuNP-siRNA-GC or AuNP-siRNA-GT delivery system synthesized as described above is absorbed in a lieum and is delivered to a liver was analyzed in vivo. For this purpose, the fluorescent and hydrophilic rhodamine B was bonded to glycol chitosan for coloring. The delivery system was orally administered to BALB/c nude mice 6 or 7 weeks old, and the images were captured after 12 hours (refer to FIG. 6). Referring to FIG. 6, it is recognized that a position of the delivery system changes as time elapses in vivo. This means that the delivery system is absorbed to other organs through a small intestine, and the delivery system can be absorbed to a living organism through oral administration. In addition, referring to FIGS. 7 and 8, fluorescent images of each organ after 12 hours show how much the delivery system is absorbed. Focusing on digestive canals, in the case of the AuNP-siRNA-GC delivery system, it is recognized that a considerable amount of particles remain in a stomach. However, in the case of the AuNP-siRNA-GT delivery system, it is recognized that an amount of drugs are absorbed in the vicinity of a lieum which is an end of a small intestine. In addition, as the conjugation ratio of TCA in the AuNP-siRNA-GT delivery system increases, the absorption increases. This is an effect of the TCA. In addition, this means the complex is absorbed through a Ileum of a small intestine, which is the same path as that of the bile acid, and is finally absorbed to a liver. Furthermore, it was recognized that the absorption of the AuNP-siRNA-GT delivery system increases when the conjugation ratio of TCA is set to 1:100 rather than 1:50. In addition, the remaining drug amount in a stomach was also negligible. Moreover, it was observed that a fluorescence level is very low in organs other than a liver, such as a heart, a lung, and a kidney. Therefore, it was recognized that the AuNP-siRNA-GT delivery system is discharged without being absorbed to other organs inside a living organism.

Conclusion

A stable AuNP-siRNA-GT delivery system was successfully manufactured by coating AuNP and thiolated siRNAs with a GT polymer. The manufactured AuNP-siRNA-GT delivery system was orally administered to a nude mouse to check absorption and movement of the AuNP-siRNA-GT delivery system. As a result, it was recognized that the AuNP-siRNA-GT delivery system is absorbed through a lieum portion of a small intestine which is the same absorption path as that of bile acid and moves specifically to a liver. This means that the AuNP-siRNA-GT delivery system according to the present invention can be effectively absorbed to a living organism through oral administration, and it can move to a liver by enterohepatic circulation inside a living organism and provide liver-organospecificity. It was also recognized that the delivery system attached with only the GC polymer does not easily move to a liver and remains in a stomach. In addition, as the conjugation ratio of TCA increases, absorption to a lieum is promoted, and movement to a liver is improved. Furthermore, it was observed that a fluorescent level in organs other than a liver, such as a heart, a lung, and a kidney, is very low. This means that a drug is discharged without being absorbed to other organs inside a living organism. This suggests that a side effect such as organ toxicity, that may be generated when the AuNP-siRNA-GT delivery system is absorbed to other organs and remains, can be minimized.

Although exemplary embodiments of the present invention have been shown and described hereinbefore, it will be apparent to those having ordinary skill in the art that a number of changes, modifications, or alterations to the invention as described herein may be made, none of which depart from the spirit of the present invention. All such changes, modifications and alterations should therefore be seen as within the scope of the present invention.

What is claimed is:

1. A metal-nanoparticle-based liver-specific nucleic acid delivery system comprising:
   (a) a metal nanoparticle;
   (b) a nucleic acid molecule bonded to a surface of the metal nanoparticle; and
   (c) a bile acid-glycol chitosan polymer attached to the nucleic acid molecule.

2. The metal-nanoparticle-based liver-specific nucleic acid delivery system according to claim 1, wherein the nucleic acid molecule is bonded to the surface of the metal nanoparticle by using a thiol group (—SH).

3. The metal-nanoparticle-based liver-specific nucleic acid delivery system according to claim 1, wherein the metal nanoparticle includes a gold nanoparticle, a silver nanoparticle, or a magnetic nanoparticle.

4. The metal-nanoparticle-based liver-specific nucleic acid delivery system according to claim 1, wherein the nucleic acid molecule is at least one molecule selected from the group consisting of deoxyribonucleic acid (DNA), ribonucleic acid (RNA), small interfering RNA (siRNA), antisense nucleic acid, nucleic acid aptamer, ribosome, polynucleotide, and oligonucleotide.

5. The metal-nanoparticle-based liver-specific nucleic acid delivery system according to claim 1, wherein the bile acid is at least one acid selected from a group consisting of deoxycholic acid, taurodeoxycholic acid, taurocholic acid, and glycochenodeoxyhoclic acid.

6. The metal-nanoparticle-based liver-specific nucleic acid delivery system according to claim 1, wherein the bile acid-glycol chitosan polymer is formed by covalent bonding between bile acid and glycol chitosan.

7. The metal-nanoparticle-based liver-specific nucleic acid delivery system according to claim 1, wherein the bile acid-glycol chitosan polymer is positively charged.

8. The metal-nanoparticle-based liver-specific nucleic acid delivery system according to claim 1, wherein a conjugation ratio between glycol chitosan and bile acid of the bile acid-glycol chitosan polymer is set to 1:1 to 1:100 as a molar ratio.

9. A liver disease treatment pharmaceutical composition containing a pharmaceutically effective amount of the nucleic acid delivery system according to claim 1.

10. A method of manufacturing a metal-nanoparticle-based liver-specific nucleic acid delivery system, the method comprising:
    (a) bonding a nucleic acid molecule to a surface of a metal nanoparticle;
    (b) reacting bile acid and glycol chitosan to produce a bile acid-glycol chitosan polymer; and
    (c) attaching the produced bile acid-glycol chitosan polymer to the metal nanoparticle having the surface where the nucleic acid molecule is bonded.

11. The method according to claim 10, wherein the metal nanoparticle includes a gold nanoparticle, a silver nanoparticle, or a magnetic nanoparticle.

12. The method according to claim 10, wherein the nucleic acid molecule is bonded to the surface of the metal nanoparticle by using a thiol group (—SH).

13. The method according to claim 10, wherein the nucleic acid molecule is at least one molecule selected from the group consisting of deoxyribonucleic acid (DNA), ribonucleic acid (RNA), small interfering RNA (siRNA), antisense nucleic acid, nucleic acid aptamer, ribosome, polynucleotide, and oligonucleotide.

14. The method according to claim 10, wherein the bile acid is at least one acid selected from the group consisting of deoxycholic acid, taurodeoxycholic acid, taurocholic acid, and glycochenodeoxyhoclic acid.

* * * * *